(12) United States Patent
March et al.

(10) Patent No.: US 9,791,363 B2
(45) Date of Patent: Oct. 17, 2017

(54) SENSOR ARRANGEMENT WITH MULTIPLE SENSORS FOR WEATHERING APPARATUS

(71) Applicant: ATLAS MATERIAL TESTING TECHNOLOGY GMBH, Linsengericht-Altenhasslau (DE)

(72) Inventors: Peter March, Frankfurt a. Main (DE); Bernd Rudolph, Alzenau (DE)

(73) Assignee: ATLAS MATERIAL TESTING TECHNOLOGY GMBH, Linsengericht-Altenhasslau (DE)

( * ) Notice: Subject to any disclaimer, the term of this patent is extended or adjusted under 35 U.S.C. 154(b) by 51 days.

(21) Appl. No.: 14/810,128

(22) Filed: Jul. 27, 2015

(65) Prior Publication Data
US 2016/0041084 A1 Feb. 11, 2016

(30) Foreign Application Priority Data

Aug. 7, 2014 (EP) .................................... 14180157

(51) Int. Cl.
*G01N 17/00* (2006.01)

(52) U.S. Cl.
CPC ......... *G01N 17/002* (2013.01); *G01N 17/004* (2013.01); *G01N 17/006* (2013.01)

(58) Field of Classification Search
CPC ... G01N 17/002; G01N 17/004; G01N 17/006
See application file for complete search history.

(56) References Cited

U.S. PATENT DOCUMENTS

| 2004/0123682 | A1* | 7/2004 | Grossman | G01N 17/002 73/865.6 |
| 2009/0064803 | A1* | 3/2009 | Pettit | G01D 21/00 73/866.5 |
| 2011/0224905 | A1* | 9/2011 | Hardcastle, III | G01W 1/00 702/3 |

FOREIGN PATENT DOCUMENTS

| EP | 1 624 297 A2 | 2/2006 |
| EP | 1 724 565 A1 | 2/2006 |
| EP | 1 710 559 A2 | 10/2006 |
| JP | 2004-145257 | 5/2004 |
| JP | 2005-308648 | 11/2005 |
| JP | 3124486 | 7/2006 |
| WO | 2005/010768 A1 | 2/2005 |
| WO | 2014/091660 A1 | 6/2014 |

OTHER PUBLICATIONS

European Search Report dated Dec. 4, 2014, in corresponding European Patent Application No. 14 180 157.1.
Japanese Office Action dated Jul. 5, 2016 in corresponding Japanese Patent Application No. 2015-155699.
Office Action issued by the Japanese Patent Office dated Feb. 28, 2017 in corresponding Japanese patent application No. 2015-155699.

* cited by examiner

*Primary Examiner* — Paul West
(74) *Attorney, Agent, or Firm* — Staas & Halsey LLP (57) ABSTRACT

The sensor device (100) has a sensor housing (110), to which at least two sensors from a group consisting of a black standard sensor (120), a UV radiation sensor (130), an air temperature sensor and a humidity sensor are connected.

15 Claims, 9 Drawing Sheets

SENSOR ARRANGEMENT WITH MULTIPLE SENSORS FOR WEATHERING APPARATUS

The present invention relates to a sensor device for an apparatus for weathering or lightfastness testing of samples and to an apparatus for weathering or lightfastness testing of samples.

In apparatuses for artificial weathering, evaluation of the weathering-related aging behavior of a sample, in particular of a flat material sample, is implemented, wherein the sample is subjected to artificial weathering. For this purpose, such apparatuses generally have a weathering chamber, in which holding means for holding samples to be weathered and a radiation source for applying radiation, in particular UV radiation, to the samples are arranged.

In such apparatuses for artificial weathering or lightfastness testing of material samples, the intention is usually to estimate the life of materials which, when in use, are continuously subjected to the natural weather conditions and therefore deteriorate under chromatic influences such as sunlight, solar heat, moisture or the like. In order to obtain an effective simulation of the natural weathering conditions, it is advantageous if the spectral energy distribution of the light generated in the apparatus corresponds as far as possible to that of natural solar radiation, for which reason xenon gas discharge lamps can be used as radiation source in such devices. In addition, accelerated aging testing of the materials is essentially achieved by irradiation of the samples which is much more intensive than the natural conditions, as a result of which the aging of the samples is accelerated. Therefore, after a comparatively short time, it is possible to draw a conclusion on the long-term aging behavior of a material sample.

The object of the present invention consists in specifying an improved apparatus for weathering or lightfastness testing of samples, in particular such an apparatus with an improved sensor system. This object is achieved by the features of the independent patent claims. Advantageous developments and embodiments are specified in the dependent claims.

The invention will be explained in more detail below with reference to exemplary embodiments in conjunction with the figures in the drawing, in which:

FIGS. 1A, B show a cross section (A) and a longitudinal section (B) through an embodiment of an apparatus for artificial weathering or lightfastness testing comprising a number of samples to be weathered and a carried-along sensor device.

In the following detailed description, reference is made to the attached drawings, which form part of this description and in which specific embodiments in which the invention can be implemented are shown for illustrative purposes. In this regard, directional terminology such as "at the top", "at the bottom", "at the front", "at the rear", "front", "rear", etc. is used with reference to the orientation of the figure(s) described. Since components of embodiments of the present invention can be positioned in a number of different orientations, the directional terminology is for illustrative purposes and is in no way restrictive. It goes without saying that other embodiments can be used and structural or logical changes made without departing from the scope of protection of the present invention. The following detailed description should therefore not be interpreted in a restrictive sense and the scope of protection of the present invention is defined by the attached claims.

A large proportion of the material samples investigated in weathering devices consist of polymeric materials. In such materials, the weathering-related deterioration is caused substantially by the UV content of the solar radiation. The photochemical primary processes occurring in the process, i.e. the absorption of photons and the generation of excited states of free radicals, are temperature-independent. On the other hand, the following reaction steps with the polymers or additives can be temperature-dependent, with the result that the observed aging of the materials is likewise temperature-dependent. The degree of temperature dependence is dependent on the material to be investigated and the property change in question.

In order to take this fact into account, the room temperature and/or the sample temperature can be kept constant in the case of artificial weathering of polymeric materials. Keeping the temperatures constant and knowledge of the temperatures are of significance owing to the temperature dependence of the aging in order to be able to compare the results of various weathering runs with one another.

Since it is problematic to measure the sample temperature of the material samples to be investigated directly, one or more temperature sensors whose measured temperature can be used as a measure of the sample temperature can be used in a weathering test device according to the invention. By way of example, black panel sensors, black standard sensors or white standard sensors can be used as such temperature sensors. If only black standard sensors are discussed below, this is intended to include all of these mentioned sensors. A weathering test device can have, for example, a weathering chamber, in which a xenon radiation source can be provided as light source for outputting light with a predetermined intensity. A cylinder-symmetrical sample holder frame, which is mounted rotatably about the radiation source, can be located within the weathering chamber. Both material samples to be investigated and black standard sensors can be borne by this sample holder frame, with the result that the material samples and the black standard sensors are subjected to the radiation field of the light source and to the remaining conditions set within the weathering chamber under the same conditions. In order to be able to control the sample temperature within specific limits and in order to make this sample temperature more uniform within the weathering chamber, an air flow can additionally be introduced into the weathering chamber, which air flow flows past the sample holder frame and the material samples held therein and the black standard sensor cylinder-symmetrically with respect to the radiation source. In the process, the air flow can dissipate some of the heat from the material samples and the black standard sensor. This can be utilized for temperature regulation, for example, by virtue of the temperature measured by the black standard sensor being used as a control signal for the intensity of the air flow introduced into the weathering chamber.

In a weathering test device according to the invention, however, further sensors still can also be used in order to further improve the control of weathering runs and the comparability thereof with one another. For example, the radiation power of the light source, in particular of the UV content thereof, can be detected. Furthermore, the temperature of the air flow present within the weathering chamber and the relative humidity thereof can be detected by suitable sensors. The output signals from these various sensors can then be supplied to a control device and detected and recorded continuously over the weathering run. They can also be used to intervene actively in the weathering run on the part of the control device and to change certain parameters in a targeted manner.

Apart from in the above-described apparatuses for artificial weathering, weathering tests can also be performed in so-called outdoor weathering plants. In said outdoor weathering plants, the weathering is performed under natural conditions, i.e. natural insolation, wherein the light intensity can be intensified artificially by suitable mirror arrangements.

In particular, one concept of the present application consists in specifying a sensor device for an apparatus for weathering or lightfastness testing of the samples with which a plurality of sensor functions can be combined in design terms.

A sensor device according to the invention for an apparatus for weathering or lightfastness testing of samples comprises, for example, a sensor housing, to which at least two different sensors are connected. These two different sensors are intended to be selected from a group of sensors consisting of a black standard sensor, a UV radiation sensor, an air temperature sensor and a humidity sensor. In such a sensor device, therefore, the at least two sensors would be installed in a compact form on a single sensor housing, which could be arranged at any desired point within a weathering chamber or in an outdoor weathering plant. Such a sensor housing could be fastened on the sample plane on a holding frame, for example, and could therefore be moved by a rotatable holding frame in the same way as a sample to be weathered about a radiation source. It would not be necessary for the two sensors to be fastened individually at different locations within the weathering chamber or on the holding frame. These advantages apply in the same way to stationary weathering test devices, in which the samples are held in stationary fashion in a weathering chamber. In these weathering test devices too, a sensor device according to the invention could be held in the same way as a sample to be weathered and could be subjected to the radiation and the other artificially produced weathering conditions.

More than two sensors, in particular more than two sensors from the mentioned group, can also be fitted in or on the sensor housing.

In accordance with one embodiment of the sensor device, a black standard sensor is fastened on an exterior wall of the sensor housing. In this case, the exterior wall can be formed by a plate, which is spaced apart from a first outer wall of the sensor housing. Then, radiation passage openings for the passage of UV radiation can be formed in this plate and in the first outer wall. The sensor housing can in particular have a right-parallelepipedal basic shape, wherein the plate can be rectangular and can have substantially the same dimensions as the first outer wall. It can be fastened at its four corners to the first outer wall by means of four screws, wherein the screws are guided within spacer sleeves, which are located between the plate and the first outer wall and ensure the desired spacing between the plate and the first outer wall.

In accordance with one embodiment of the sensor device, an air passage opening for the passage of ambient air to the air temperature sensor and the humidity sensor can be formed in the first outer wall or possibly also in another outer wall of the sensor housing. If the air passage opening is formed in the first outer wall of the sensor housing, this would have the advantage that it could be shielded from the radiation of the radiation source during operation of the weathering chamber, namely by virtue of the plate which is held spaced apart covering the air passage opening. This would automatically be the case if the plate, as described above, were to have substantially the same outer dimensions as the first outer wall of the sensor housing.

In accordance with one embodiment of the sensor device, an electrical power supply, such as a battery or a rechargeable battery, is arranged within the sensor housing. This electrical power supply is connected to a circuit and supplies the necessary electrical voltages both to the components of the circuit and to the sensors.

In accordance with one embodiment of the sensor device, a first circuit board is arranged within the sensor housing, with it being possible for a control unit to be arranged on said circuit board, to which control unit output signals from the sensors can be supplied. Provision can furthermore be made for a first memory unit on which data specific to the UV radiation sensor is stored to be arranged on the first circuit board. The first memory unit can have, for example, a DRAM, in particular a ferroelectric DRAM (FRAM). In addition, the control unit can have a second memory unit on which data specific to a radiation source of the apparatus, in particular a xenon radiation source, is stored.

In accordance with one embodiment of the sensor device, the air temperature sensor and the humidity sensor are arranged in a common housing, which is arranged within the sensor housing. The common housing can have a vapor-permeable and/or microporous membrane for the passage of air to the two sensors.

In accordance with one embodiment of the sensor device, the UV radiation sensor can be designed in such a way that it generates a cosine-corrected measurement signal and transmits this to the control unit. This means that the sensor is designed to take into consideration the dependence of the measured radiation intensity on the angle between the impinging radiation and the surface normal of the sensor or a pixel of the sensor or to generate a measurement signal which takes into consideration or corrects this dependence. In a simple variant, this can be implemented in such a way that the UV radiation sensor has a housing comprising an inlet opening and a diffuser arranged in the inlet opening. A UV radiation sensor with such a design can then be arranged in the radiation passage openings in the plate and the outer wall of the sensor housing in such a way that the inlet opening in the housing and the diffuser are located outside the plate and are protected from the surrounding environment by a hemispherical protective wall consisting of quartz glass.

In accordance with one embodiment of the sensor device, said sensor device is designed for transmitting the output signals from the sensors to a central control unit, by means of which the weathering runs can also be controlled, for example. The sensor device can be designed in particular for wired transmission of the output signals from the sensors, for which purpose the sensor device can have a USB interface, for example. In the case of weathering test devices having a rotatable holding frame, the sensor device is moved constantly by the holding frame around the radiation source in the same way as the samples to be weathered. In this case, provision can be made for the sensor device to be coupled to a slipring arrangement, via which the output signals from the sensors are transmitted to the central control unit. In accordance with an embodiment which represents an alternative to this, provision can also be made for the sensor device to be configured for wireless transmission of the output signals from the sensors to the central control unit.

In accordance with one embodiment of the sensor device, the housing is designed in terms of its external dimensions in such a way that it can be fastened, in the same way as the sample to be weathered, within the weathering chamber or on an outdoor weathering plant so that the black standard sensor faces the radiation source. In general, correspondingly designed receiving elements or receiving devices are arranged in such apparatuses, with it being possible for the samples to be weathered to be received and fastened suitably in or on said receiving elements or receiving devices. Accordingly, it can be provided that the sensor device can be held or fastened on precisely the same receiving elements or receiving devices without additional measures needing to be taken.

The invention likewise relates to an apparatus for weathering or lightfastness testing of samples comprising a holding device for holding samples to be weathered and a sensor device, which has a sensor housing, to which a plurality of sensors, in particular an air temperature sensor and humidity sensor, are connected. The sensor device can be configured in particular as has already been described above.

In accordance with one embodiment of the apparatus, output signals from the sensors can be transmitted to a central control unit, wherein in addition provision can be made for weathering runs to be controlled, or their sequence changed, by the central control unit depending on the output signals from the sensors. In the case of an apparatus for artificial weathering, the central control unit is arranged outside the weathering chamber and is provided, for example, by a PC and the control software thereof.

In accordance with one embodiment of the apparatus, the air temperature sensor and the humidity sensor are arranged in a common housing, which is arranged within the sensor housing. The further configuration can be as has already been described above with reference to the sensor device.

In accordance with one embodiment of the apparatus, the sensor device also has a black standard sensor and a UV radiation sensor, which are connected to the sensor housing. The further configuration of said sensors can also correspond to that which has already been described above with reference to the sensor device.

In accordance with one embodiment of the apparatus, said apparatus has a central control device such as a PC for controlling a weathering operation, wherein output signals from at least one of the mentioned sensors can be supplied to the central control device. The central control device can in particular be designed to receive such output signals using wires. It can alternatively also be designed to receive the output signals wirelessly.

In accordance with one embodiment of the apparatus, said apparatus has receiving elements or receiving devices, which are designed in such a way that the samples to be weathered can be received or fastened in or on said receiving elements or receiving devices. Provision can be made for these receiving elements and receiving devices to likewise be suitable for receiving and fastening a sensor device, so that in this regard there is no difference between receiving devices which receive a sample to be weathered and a sensor device.

In accordance with one embodiment of the apparatus, said apparatus is designed in such a way that it has a weathering chamber, in which artificial weathering or lightfastness testing of samples can be implemented. In this case, provision can be made for the holding device to be formed rotatably about a radiation source so that the samples and with them also the sensor device are in constant rotary motion around the radiation source during a weathering run. However, provision can also be made for the samples to be weathered to be held in stationary fashion and therefore not to be in constant motion during a weathering run.

In accordance with one embodiment of the apparatus, said apparatus is in the form of an apparatus for outdoor weathering of samples. In this case, the weathering accordingly does not take place within a closed weathering chamber but under natural conditions, in particular natural insolation. The latter can be artificially intensified by suitable mirror arrangements, if desired.

Figure 1:
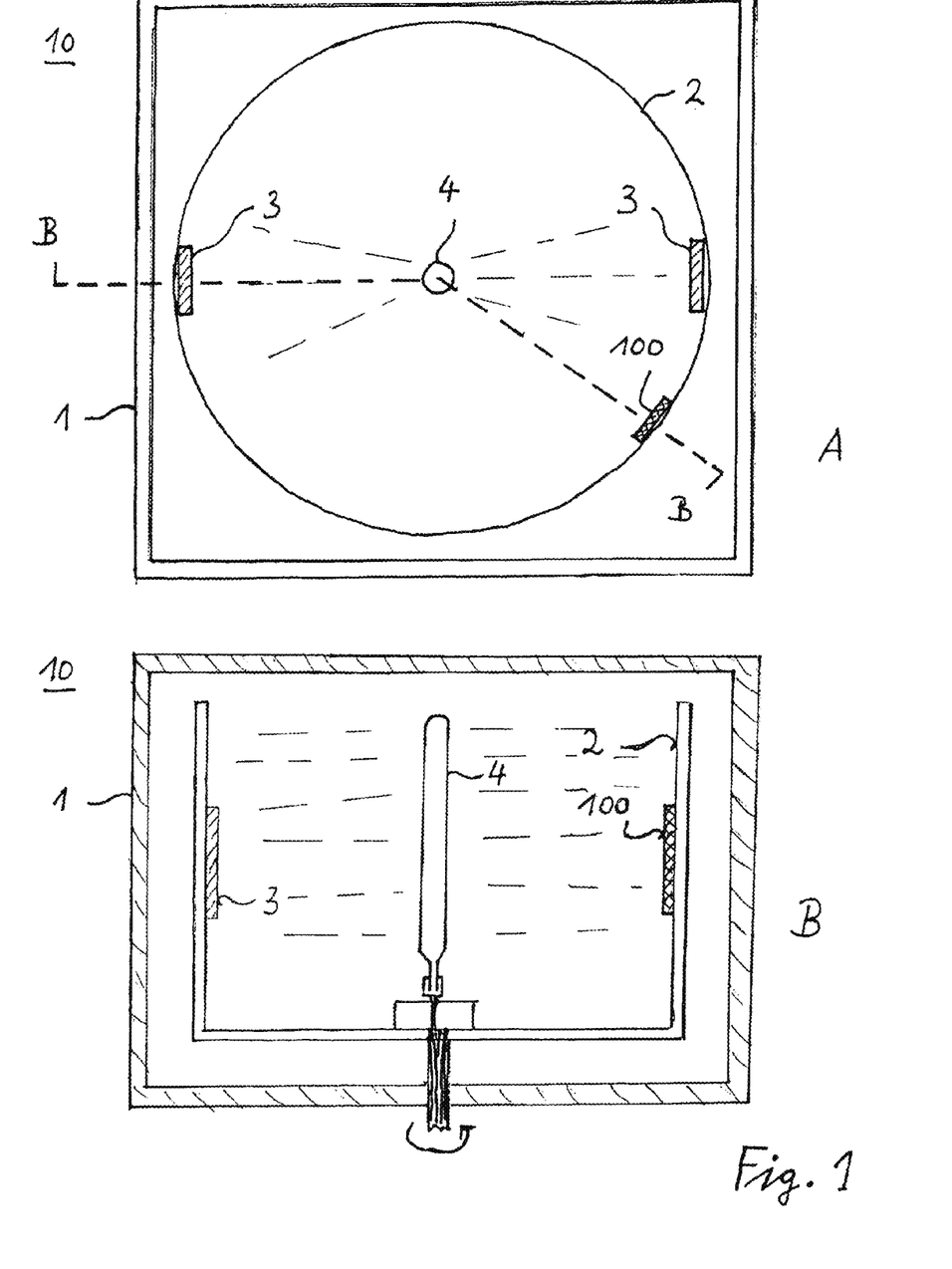

FIGS. 1A, B show an embodiment of an apparatus for artificial weathering or lightfastness testing of samples in a cross section (A) and a longitudinal section (B) along the dashed line B-B illustrated in FIG. 1A, in each case schematically. The apparatus 10 comprises a weathering chamber 1, within which artificial weathering or lightfastness testing of samples can be implemented. A holding frame 2 closed in the form of a ring is mounted rotatably in the weathering chamber 1 and has suitably shaped holding elements (not shown) on its inner side, by means of which holding elements samples 3 or workpieces, for example rectangular paint samples of standardized size, can be held. The holding frame 2 is in particular circular in a lateral cross section, with the result that the samples 3 are guided on a closed circular path during rotation of the holding frame 2. A radiation source 4, which can be formed by a xenon discharge lamp, for example, is arranged within the holding frame 2 and substantially concentrically with respect thereto. It can be provided that a plurality of samples 3 can be fastened on the holding frame 2, in particular on holding elements provided for this purpose and arranged in the circumferential direction of the holding frame 2. Furthermore, the samples 3 can also be fastened in a plurality of planes one above the other on the holding frame 2.

Furthermore, a sensor device 100, which can perform various sensor functions, can be arranged in the weathering chamber 1. In particular, said sensor device can be designed to detect the radiation power of the radiation emitted by the radiation source 4 and/or other variables such as the sample temperature, the air temperature and the humidity. The sensor device 100 can be fastened on the holding frame 2 in the same way as the samples 3 and revolve with said holding frame around the arrangement consisting of the radiation source 4, i.e. can be formed as a carried-along sensor device 100. The output signals from the sensor device 100 can be supplied to an external central control device. In particular, the sensor device 100 can be designed in such a way that the parameters detected by said sensor device are output as corresponding electrical measurement signals and supplied to the external central control device. The sensor device 100 can, as illustrated, be arranged offset with respect to the samples 3 in the circumferential direction of the holding device 2. The sensor device could just as easily also be arranged without any circumferential offset in the vertical direction with respect to the samples 3 or so as to be offset both in the vertical and in the circumferential direction with respect to the samples 3.

The weathering chamber 1 can have further devices for artificial weathering, such as moisture generators or the like, for example, which will not be discussed in any more detail below. An air flow can also be introduced into the weathering chamber 1, for example, which air flow flows past the samples 3 and/or the radiation source 4 in the vertical direction.

Figure 2:
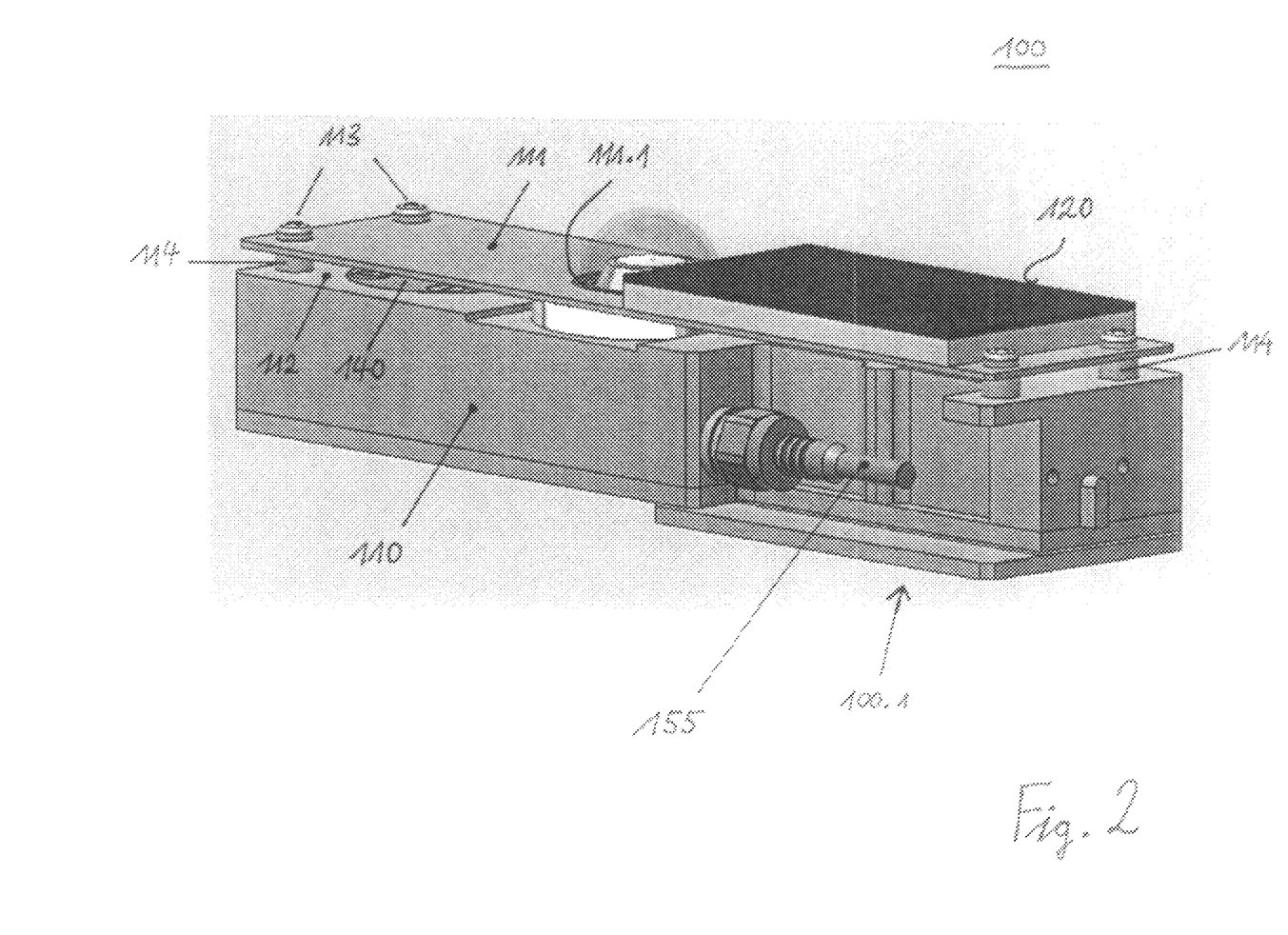
FIG. 2 shows a perspective view of a sensor device in accordance with one embodiment.

FIG. 2 shows a perspective illustration of an embodiment of a sensor device 100. The sensor device 100 contains a sensor housing 110 consisting of stainless steel, which has a substantially right-parallelepipedal basic shape. In front of a first outer wall 112 of the sensor housing 110, a plate 111 is fastened on the first outer wall 112 spaced apart therefrom. The fastening can be performed, as illustrated, by screws 113 arranged in the region of the four corners of the plate 111, which screws are passed through spacer sleeves 114 between the plate 111 and the first outer wall 112 and are screwed into corresponding bores in the region of the four corners of the first outer wall 112. A black standard sensor 120 is fastened on the plate 111 and, during running operation of a weathering apparatus, faces the radiation source of the weathering apparatus.

The black standard sensor 120 can be constructed in such a way that it has a stainless steel plate with a surface painted black which faces the radiation source during operation and a temperature-dependent electrical component coupled thermally to the stainless steel plate on the rear side thereof. The electrical component can be formed by a temperature-dependent resistor such as a platinum resistor (commercially available designations Pt100 or Pt1000) and can be connected to an electrical measuring transducer circuit. In particular, a plastic plate consisting of PVDF (polyvinylidene fluoride) which surrounds the platinum resistor and a termination plate consisting of stainless steel can be fitted on the rear side of the stainless steel plate. A black panel sensor, in contrast to the black standard sensor, consists of a metal plate which is blackened on both sides without any PVDF insulation, wherein the temperature-dependent resistor is applied to the rear side of the stainless steel plate without any surrounding insulation. Such black standard or black panel sensors can be used in weathering devices in order to be able to give a black standard temperature for each weathering process. The black standard temperature represents an upper limit for the possible range of the surface temperature of the material sample. In addition, a white standard sensor can be used, whose temperature measurement provides a lower limit of this range. Therefore, the sample temperature can be limited and, possibly as a first approximation for the sample temperature, the arithmetic mean of the measured temperatures can be assumed.

The sensor device 100 also has a cutout 100.1, in which an electrical plug-type connector 155 is arranged, which is passed through a side wall of the cutout 100.1 and is connected to a first circuit board 160 in the interior of the sensor housing 110, as will be shown further below. Output signals from the sensors can be transmitted over wires to a central control device of the weathering apparatus 10 via the electrical plug-type connector 155. The data transmission can take place by means of a serial bus system, which is based on the USB standard, for example. The electrical plug-type connector 155 is advantageously oriented in the longitudinal direction in the cutout 100.1, with the result that a cable connected to the electrical plug-type connector 155 can be passed away from the sensor device 100 in the longitudinal direction.

Figure 3:
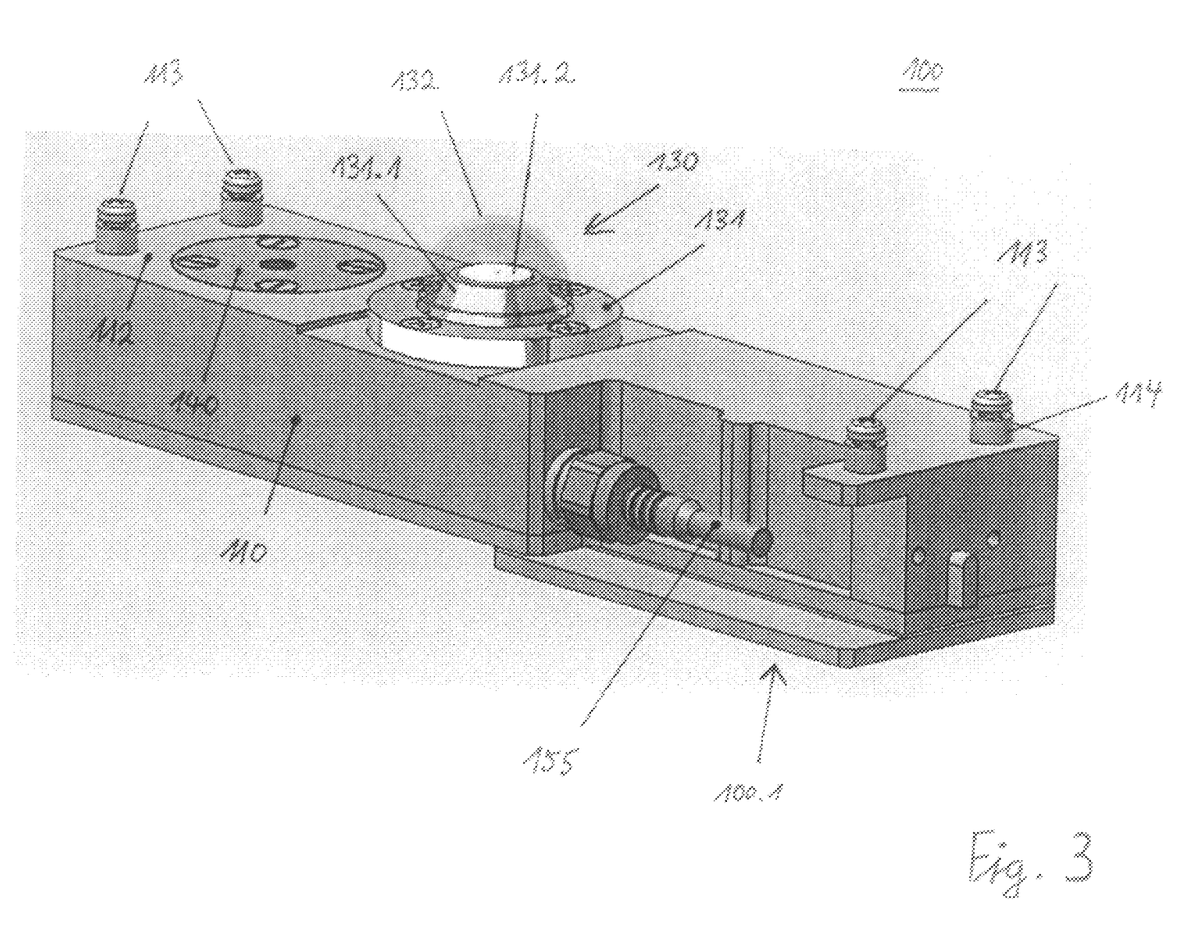
FIG. 3 shows the sensor device shown in FIG. 2 with the plate removed.

FIG. 3 shows a perspective view of the sensor device 100 once the plate 111 and the black standard sensor 120 arranged thereon have been removed. The sensor device 100 can accordingly have yet further sensors, which can likewise be arranged on the first outer wall 112 of the sensor housing 110. A UV radiation sensor 130 is arranged adjacent to the black standard sensor 120 and therefore in the inserted state faces the sensor device 100 and during operation of the weathering apparatus 10 likewise faces the radiation source 4. The UV radiation sensor 130 or the upper part thereof is fitted within a first flange 131, which has a central circular cutout, within which an upwardly tapering elevation 131.1 in the form of a truncated cone is arranged, which elevation has an inlet opening at its upper flattened end, in which opening a diffuser 131.2 is arranged. The diffuser 131.2 ensures cos φ correction of the incoming radiation, as has already been explained further above. The inlet opening is located above the upper surface of the first flange 131. A hemispherical protective wall 132 consisting of quartz glass is arranged around the elevation 131.1 in the form of a truncated cone and is inserted with its lower rim into the recess in the first flange 131. An opening 111.1 is formed in the plate 111, as can be seen in FIG. 2, in the region of the UV radiation sensor 130, with the upper part of the elevation 131 in the form of a truncated cone and the hemispherical protective wall 132 extending through said opening.

Figure 4:
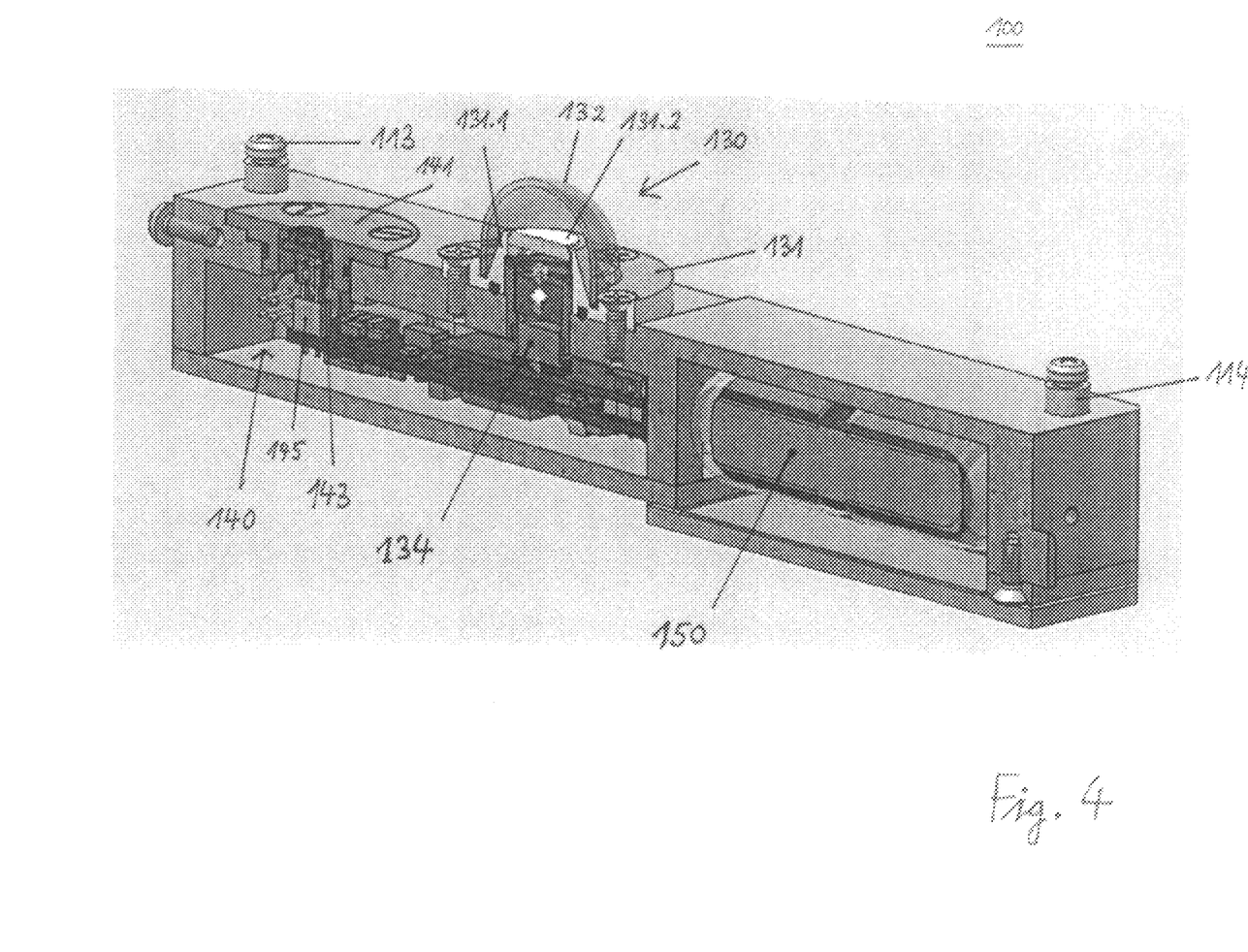
FIG. 4 shows the sensor device shown in FIG. 3 in a longitudinal section.
Figure 5:
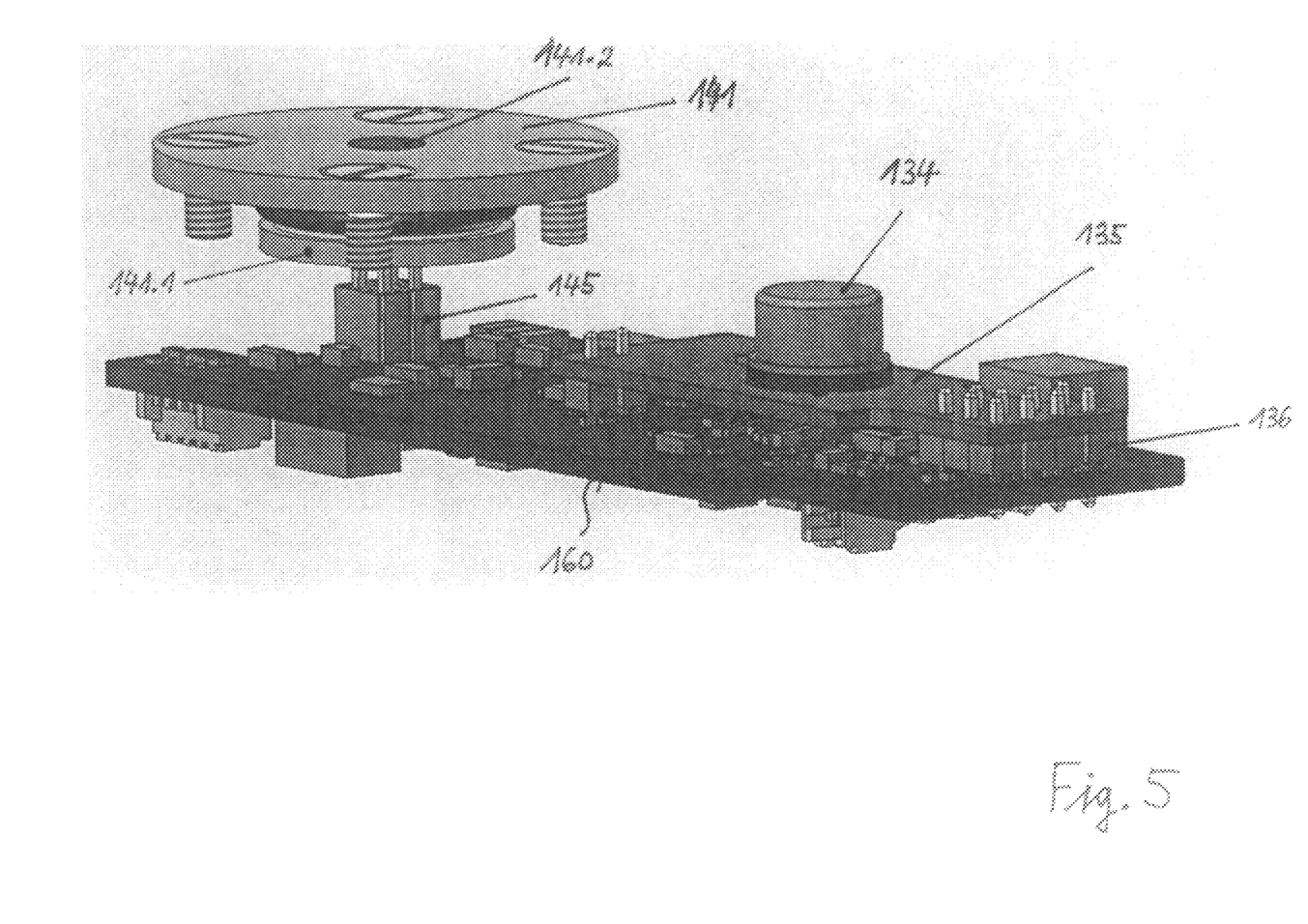
FIG. 5 shows a perspective view of a first circuit board with a sensor head fastened thereon of the combined air temperature/humidity sensor and a second circuit board with a radiation sensor fastened thereon.

FIG. 4 shows a longitudinal section through the sensor device 100, in which it can be seen that the UV radiation sensor 130 can furthermore have a standard TO5 housing 134, within which the actual light reception diode is arranged. FIG. 4 and FIG. 5 show that the TO5 housing 134 is fitted on a second circuit board 135. The UV radiation sensor 130 furthermore has a UV radiation filter, which is arranged below the diffuser 131.2 in the beam path. As can be seen from FIG. 4, the upper part of the TO5 housing 134 is arranged within an opening in the first outer wall 112 of the sensor housing 110, which opening is arranged cylinder-symmetrically with respect to the first flange 131 and the elevation 131.1 in the form of a truncated cone.

As can be seen in FIG. 3 to FIG. 5, the first flange 131 is screwed to the first outer wall 112 of the sensor housing 110 by means of four screws.

Figure 7:
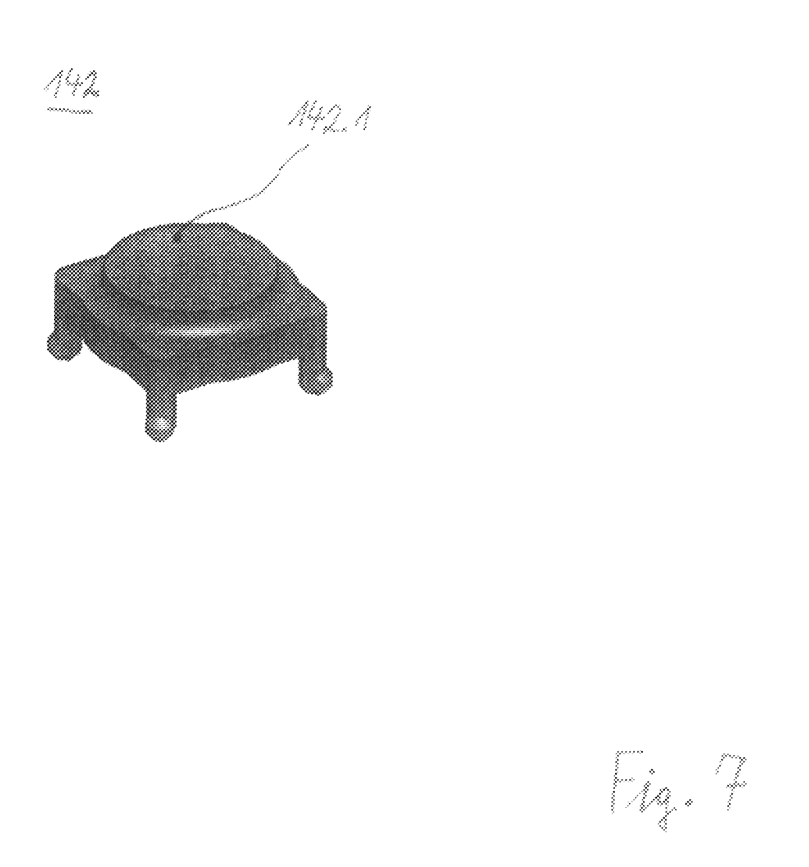
FIG. 7 shows a perspective view of a combined air temperature/humidity sensor.

As is already indicated in FIG. 2 and FIG. 3, in addition a combined air temperature/humidity sensor 140 can be arranged in the sensor housing 110, which sensor is fitted on a second flange 141. The second flange 141 can likewise be fastened to the first outer wall 112 of the sensor housing 110 using four screws. The second flange 141 is once again shown in FIG. 5 in greater detail in the left-hand half of the figure. The second flange 141 has a central opening 141.2, below which a sensor package 142, which may be commercially available, is arranged, said sensor package containing an air temperature sensor and a humidity sensor. The sensor package 142 is illustrated in enlarged form in FIG. 7. It has a vapor-permeable and/or microporous membrane 142.1 on its upper side, with it being possible for the ambient air to penetrate through said membrane to the combined sensor. In the assembled state of the sensor device 100, the plate 111 is located above the central opening 141.2 of the second flange 141 and therefore covers the inlet opening to the sensor package 142, with the result that, in the inserted state of the sensor device 100 in a weathering apparatus 10, the radiation from the radiation source 4 during operation of said weathering apparatus does not pass to the inlet opening of the sensor package 142.

Figure 6:
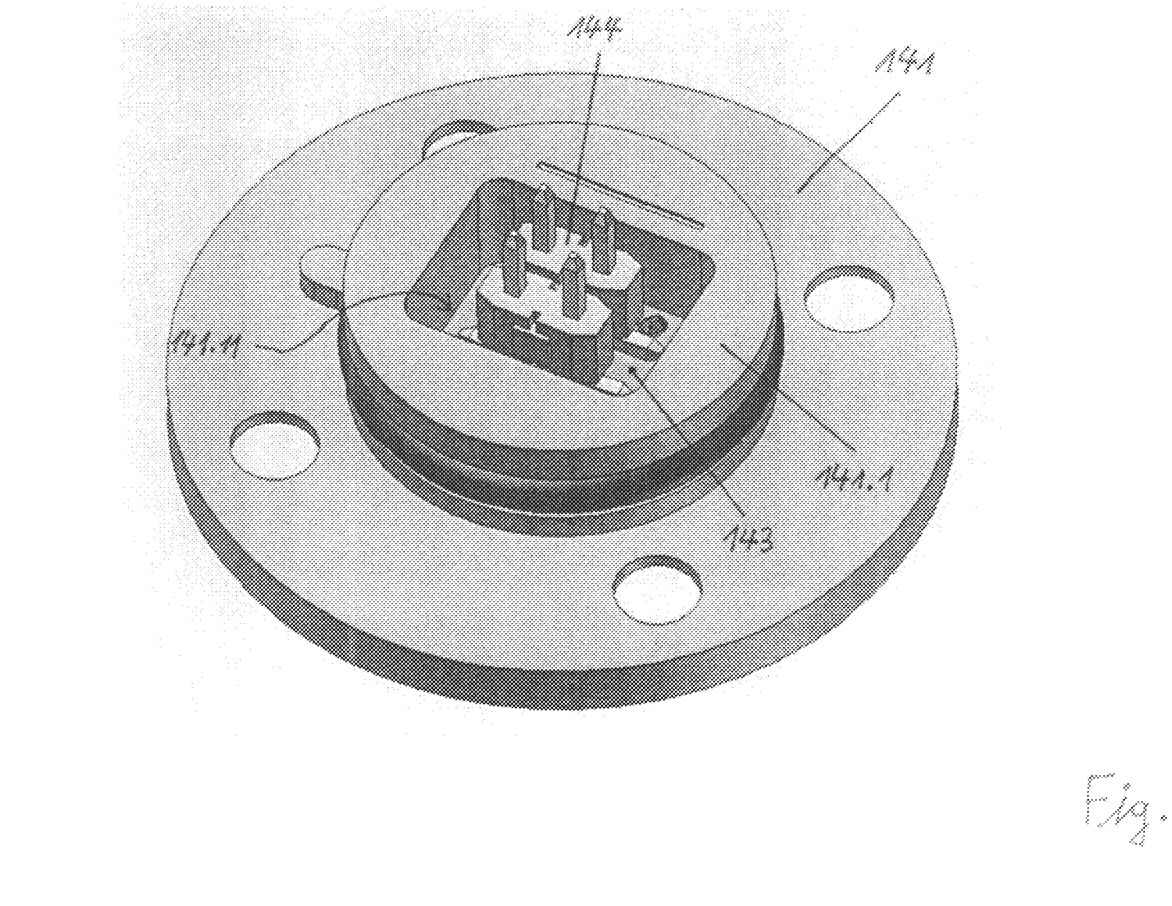
FIG. 6 shows a perspective view of a sensor head with a combined air temperature/humidity sensor fastened thereon.
Figure 8:
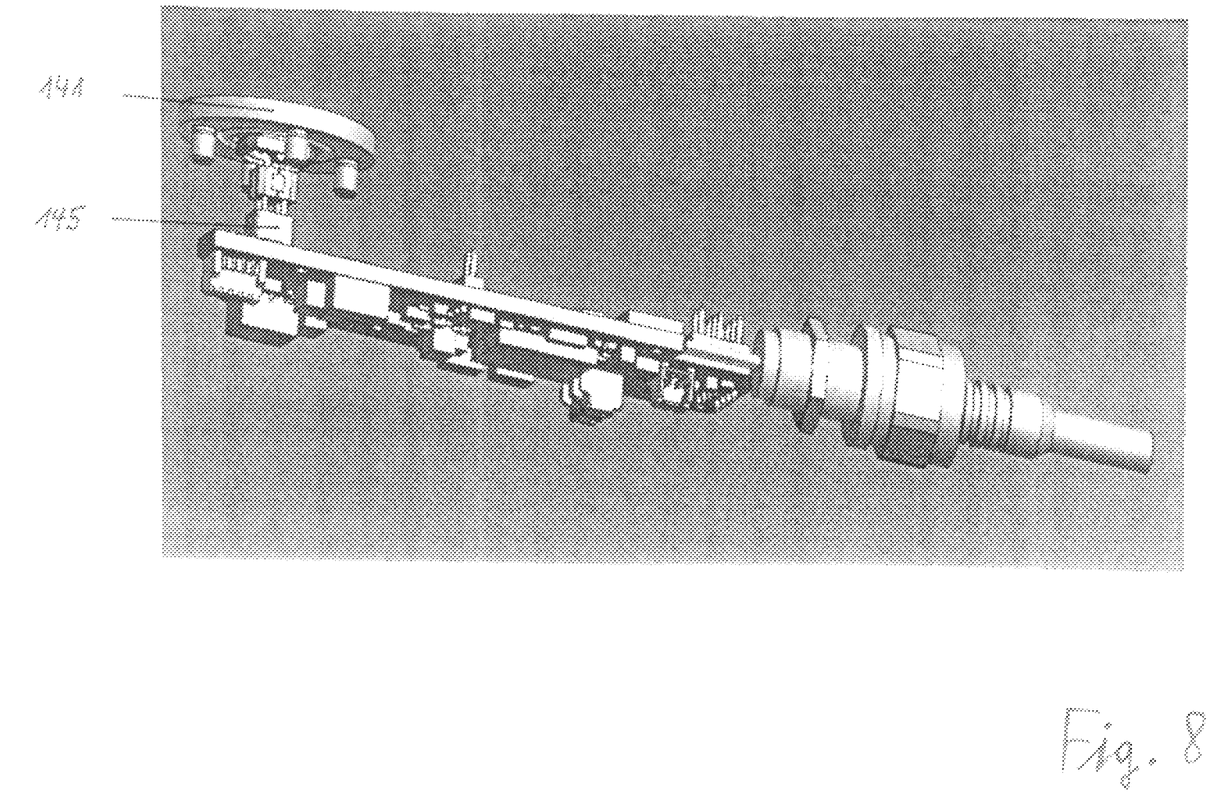
FIG. 8 shows a perspective view of a first circuit board with a sensor head fastened thereon with the combined air temperature/humidity sensor and an electrical connection, which is connected to the first circuit board.

FIG. 6 shows a perspective view of the second flange 141 from below. The second flange 141 has a central disk-shaped elevation 141.1, which has a cutout 141.11 which is rectangular in cross section, with the board 143 being arranged in the lower region of said cutout. The sensor package 142 (not shown directly in FIG. 6) is connected to the board 143 on the remote side of the board 143 in the viewing direction. On the front side of the board 143 in the viewing direction, a plug system 144 is connected to the board 143, whose plug-in contacts are connected to corresponding electrical contacts of the sensor package 142 through the board 143. The spatial region around the plug system 144 within the cutout 141.11 is potted with a potting compound, such as an epoxy resin. As can be seen in FIG. 4 and in FIG. 8 and in greater detail in FIG. 5, the plug contacts are then inserted into a plug-type connector 145, whose outputs are connected to the first circuit board 160. The second circuit board 135 for its part is likewise connected to the first circuit board 160 by means of plug-type connectors 136.

FIG. 4 also shows that the sensor device 100 can have a battery 150, which can be arranged directly beneath the black panel sensor 120 within a chamber. The battery 150 can be in the form of a high-temperature battery, i.e. can be rated for a temperature of up to 80° C., for example. The battery 150 acts as electrical power supply for the sensors and for the electrical circuit and the components contained therein, such as the control device, memory, etc.

Figure 9:
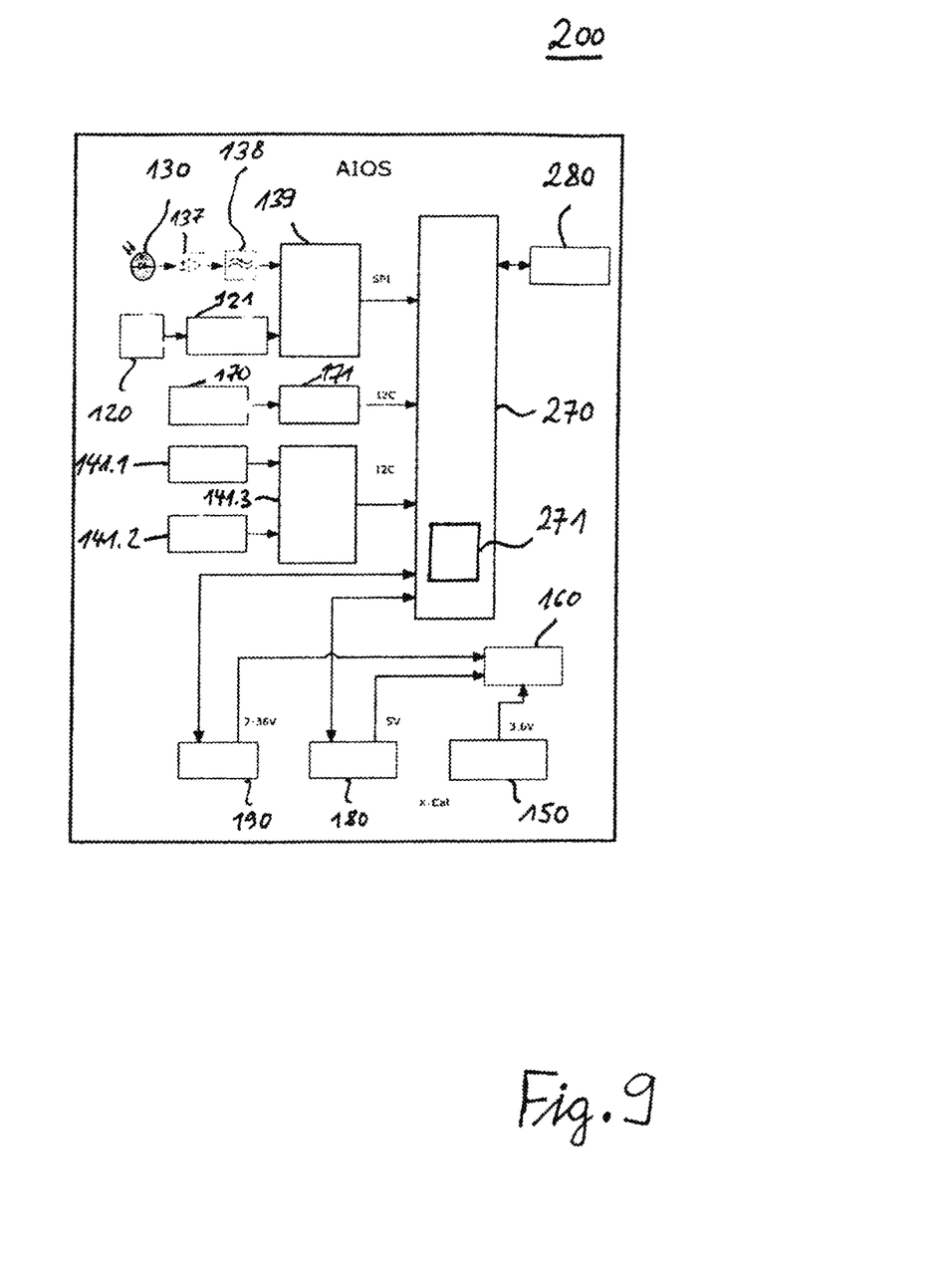
FIG. 9 shows a block circuit diagram of an electrical circuit of a sensor device.

FIG. 9 shows a block circuit diagram of an electrical circuit of a sensor device. The circuit 200 illustrated contains electrical components, as are applied on the electrical circuit boards 135 and 160. The circuit 200 has a control unit 270, to which output signals from the sensors can be supplied. The control unit 270 can be formed by a microprocessor or microcontroller with a design known per se. A first memory unit 280 on which data specific to the UV radiation sensor 130 can be stored is connected to the control unit 270. The first memory unit 280 can be formed by a DRAM, in particular a ferroelectric DRAM (FRAM). The control unit 270 can furthermore have a second memory unit 271 on which data specific to a radiation source of the weathering apparatus can be stored. The control unit 270 can be fitted on the first circuit board 160. The UV radiation sensor 130 is connected on the output side to an amplifier 137 and a low-pass filter 138, whose output is connected to an analog-to-digital converter 139. The black standard sensor 120 is connected on the output side to a signal conditioning circuit 121, whose output is connected to the analog-to-digital converter 139. The analog-to-digital converter 139 is connected on the output side to the control unit 270. An air temperature sensor 141.1 and a humidity sensor 141.2 are each connected to a data processor 141.3 on the output side, the output of said data processor being connected to the control unit 270. A further temperature sensor 170 is arranged on one of the circuit boards, connected on the output side to a signal conditioning circuit 171, which is for its part connected on the output side to the control unit 270. In addition, a battery 150, a power supply/power control circuit 160 connected to the battery 150, a USB interface 180 connected to the circuit 160 and a 485/422 interface 190 connected to the circuit 160 are included in the circuit 200.

Although specific embodiments have been illustrated and described in this description, a person skilled in the relevant art should be aware that the specific embodiments shown and described can be replaced by a multiplicity of alternative and/or equivalent implementations without departing from the scope of protection of the present invention. This application is intended to cover any amendments or changes to the specific embodiments set forth herein. Therefore, provision is made for this invention to only be limited by the claims and equivalents thereof.

The invention claimed is:

1. A sensor device for an apparatus for weathering or lightfastness testing of samples, comprising:
   a sensor housing, to which at least two sensors from a group consisting of
   a black panel sensor or a black standard sensor,
   a UV radiation sensor,
   an air temperature sensor, and
   a humidity sensor are connected, wherein
   the sensor housing comprises an exterior wall, and
   one sensor of the at least two sensors is a black panel sensor or a black standard sensor and the black panel sensor or the black standard sensor is fastened to an outside of the exterior wall of the sensor housing so as to face an outside of the sensor housing.

2. The sensor device as claimed in claim 1, in which the exterior wall of the sensor housing is formed by a plate, which is spaced apart from a first outer wall of the sensor housing.

3. The sensor device as claimed in claim 2, in which radiation passage openings for the passage of UV radiation are formed in the plate and in the first outer wall.

4. The sensor device as claimed in claim 1, in which an air passage opening for the passage of ambient air to an air temperature sensor and a humidity sensor is formed in an outer wall of the sensor housing.

5. The sensor device as claimed in claim 4, in which a plate, which is spaced apart from the outer wall of the sensor housing, covers the air passage opening.

6. The sensor device as claimed in claim 1, in which a battery or a rechargeable battery is arranged within the sensor housing.

7. The sensor device as claimed in claim 1, in which a first circuit board is arranged within the sensor housing, with a control unit being arranged on the first circuit board, to which control unit output signals from the sensors can be supplied.

8. The sensor device as claimed in claim 7, in which one sensor of the at least two sensors is a UV radiation sensor, and a first memory unit on which data specific to the UV radiation sensor is stored is arranged on the first circuit board.

9. The sensor device as claimed in claim 8, in which the first memory unit has a DRAM.

10. The sensor device as claimed in claim 9, in which the DRAM is a ferroelectric DRAM (FRAM).

11. The sensor device as claimed in claim 8, in which the control unit has a second memory unit, on which data specific to a radiation source of the apparatus is stored.

12. An apparatus for weathering or lightfastness testing of samples, comprising:
   a holding device to hold samples to be weathered;
   a sensor device, which comprises a sensor housing, the sensor housing comprising an exterior wall; and
   a plurality of sensors connected to the sensor housing, wherein
   one sensor of the plurality of sensors is a black panel sensor or a black standard sensor and the black panel sensor or the black standard sensor is fastened to an outside of the exterior wall of the sensor housing so as to face an outside of the sensor housing.

13. The apparatus as claimed in claim 12, in which the plurality of sensors comprises an air temperature sensor and a humidity sensor, and the air temperature sensor and the humidity sensor are arranged in a common housing, which is arranged within the sensor housing.

14. The apparatus as claimed in claim 12, in which the plurality of sensors comprises a UV radiation sensor.

15. The apparatus as claimed in claim 12, further comprising
   a central controller configured to control a weathering operation, to which controller output signals from at least one of the plurality of sensors can be supplied.

\* \* \* \* \*